(12) United States Patent
Hayashi et al.

(10) Patent No.: US 9,675,538 B2
(45) Date of Patent: Jun. 13, 2017

(54) ANTI-AGING AGENT CONTAINING ARCTIGENIN DERIVATIVE

(71) Applicant: ROHTO Pharmaceutical Co., Ltd., Osaka-shi (JP)

(72) Inventors: Yuya Hayashi, Osaka (JP); Yoko Mizutare, Osaka (JP)

(73) Assignee: Rohto Pharmaceutical Co., Ltd., Osaka (JP)

( * ) Notice: Subject to any disclaimer, the term of this patent is extended or adjusted under 35 U.S.C. 154(b) by 300 days.

(21) Appl. No.: 14/389,200

(22) PCT Filed: Mar. 27, 2013

(86) PCT No.: PCT/JP2013/059128
§ 371 (c)(1),
(2) Date: Sep. 29, 2014

(87) PCT Pub. No.: WO2013/146943
PCT Pub. Date: Oct. 3, 2013

(65) Prior Publication Data
US 2015/0093345 A1 Apr. 2, 2015

(30) Foreign Application Priority Data
Mar. 30, 2012 (JP) .................. 2012-081177

(51) Int. Cl.
*A61K 8/00* (2006.01)
*A61K 8/49* (2006.01)
*A61Q 19/02* (2006.01)
*A61Q 19/08* (2006.01)
*A61K 31/365* (2006.01)
*C07D 307/33* (2006.01)

(52) U.S. Cl.
CPC .......... *A61K 8/4973* (2013.01); *A61K 31/365* (2013.01); *A61Q 19/02* (2013.01); *A61Q 19/08* (2013.01); *C07D 307/33* (2013.01); *A61K 2800/782* (2013.01)

(58) Field of Classification Search
CPC ............ A61K 8/4973; A61K 2800/782; A61K 31/365; A61K 8/602; A61Q 19/02; A61Q 19/08
See application file for complete search history.

(56) References Cited

U.S. PATENT DOCUMENTS

| 2007/0110704 A1 | 5/2007 | Gallinat et al. |
| 2009/0298783 A1 | 12/2009 | Danoux et al. |
| 2010/0104524 A1 | 4/2010 | Lee et al. |

FOREIGN PATENT DOCUMENTS

| CN | 101264077 A | 9/2008 |
| CN | 102342929 A | 2/2012 |
| JP | 1-228928 | 9/1989 |
| JP | 2-40323 | 2/1990 |
| JP | 2004-331547 | 11/2004 |
| JP | 3658548 | 6/2005 |
| JP | 2006-347942 | 12/2006 |
| JP | 2007-513104 | 5/2007 |
| JP | 2008-088073 A | 4/2008 |
| JP | 2009-149626 | 7/2009 |
| JP | 2010-503712 | 2/2010 |
| JP | 2010-520233 | 6/2010 |
| JP | 2012-31081 | 2/2012 |

OTHER PUBLICATIONS

Office Action in Chinese Patent Application No. 201380018075.6, issued Jan. 29, 2016.
Partial English Translation of Shigeru Sekine, "Shin Keshohin Handbook" . . . (Oct. 30, 2006) pp. 518 to 524.
Office Action in Taiwanese Patent Application No. 102111446, dated May 20, 2016.
Shigeru Sekine, "Moisturizing agent," New Cosmetics Handbook, Nikko Chemicals Co. Ltd., Oct. 30, 2006, pp. 518-524.
Shigeru Sekine, "Melanocyte activating factor," New Cosmetics Handbook, Nikko Chemicals Co. Ltd., Oct. 30, 2006, pp. 525-528.
K, Tsukahara, et al., "Wrinkle preventive effect by a fibroblast elastase specific inhibitor," Fragrance Journal, Dec. 15, 2006, pp. 36-41 and 131-137 pages.
K. Umehara, et al., "Studies on Differentiation Inducers. VI. Lignan Derivatives from Arctium Fructus." Chem. Pharm. Bull, 1996, vol. 44, No. 12, pp. 2300-2304.
The Second Office Action mailed by the State Intellectual Property Office of People's Republic of China on Oct. 25, 2016 in the corresponding Chinese patent application No. 201380018075.6—3 pages.
Notification of Reasons for Refusal mailed by Japan Patent Office on Oct. 19, 2016 in the corresponding Japanese patent application No. 2014-507985—4 pages.

*Primary Examiner* — Nannette Holloman
(74) *Attorney, Agent, or Firm* — Knobbe, Martens, Olson & Bear, LLP

(57) ABSTRACT

An arctigenin derivative used for anti-aging treatment, including protection of the skin from the sun and recovery of skin elasticity. A variety of fatty acid ester derivatives, alcohol ether derivatives and alkylated derivatives are used as the arctigenin derivatives. Agents for controlling ET-1 production, elastase inhibitors, and anti-inflammatory agents are prepared. Such arctigenin derivatives are particularly useful as an external agent for the skin, such as an anti-inflammatory external agent, a sunscreen external agent, or an external agent for recovering elasticity.

4 Claims, 10 Drawing Sheets

ANTI-AGING AGENT CONTAINING ARCTIGENIN DERIVATIVE

This application is the U.S. National Phase under 35 U.S.C. §371 of International Application No. PCT/JP2013/059128, filed Mar. 27, 2013, designating the U.S., and published in Japanese as WO 2013/146943 on Oct. 3, 2013, which claims priority to Japanese Patent Application No. 2012-081177 filed Mar. 30, 2012, the entire contents of which are incorporated herein by reference.

TECHNICAL FIELD

The present invention relates to an anti-aging agent containing an arctigenin derivative. More specifically, the present invention relates to an anti-aging agent containing an arctigenin derivative to have a skin-whitening effect, an anti-wrinkle effect or any other skin-elasticity-recovering effect, an anti-inflammatory effect, and other effects.

BACKGROUND ART

The aging of the skin of a person appears as skin sagging, wrinkles, skin dullness, liver spots, or some other to produce a remarkable effect onto the external appearance of the person. For preventing or slowing down such phenomena, a skin-care agent for anti-aging (aging resistance) has been desired.

Out of these phenomena, wrinkles and skin sagging result from the drying of keratin, or irradiation with ultraviolet rays, and are caused by changes in the tissue of the skin, such as a physical deterioration of a matrix component thereof.

The skin dullness, and liver spots are related to the configuration or composition or the quantities of skin-color-producing factors, such as melanin, hemoglobin in blood, and carotene. Out of these factors, melanin is a particularly important factor for determining the color of a skin, and causes the skin dullness, and liver spots. In other words, the color of a skin depends on the amount and the nature of melanin, and the degree of the distribution thereof. Factors for promoting the production of melanin are ultraviolet rays and inflammation; and, in particular, ultraviolet rays having short wavelengths (290 to 320 nm) produce a large influence.

As anti-aging agents, substances each originating from a natural component have also been researched. One of the substances is a substance named arctigenin, which is a kind of lignin contained in Saussurea laniceps (medusa) or cherry bark. It has been known that arctigenin has a skin-whitening effect, and skin-barrier-performance-improving and other effects (Patent Documents 1 to 6).

PRIOR ART DOCUMENTS

Patent Documents

Patent Document 1: JP-A-2010-520233
Patent Document 2: JP-A-2004-331547
Patent Document 3: Japanese Patent No. 3658548
Patent Document 4: JP-A-2007-513104
Patent Document 5: JP-T-2010-503712
Patent Document 6: JP-A-2009-149626

SUMMARY OF THE INVENTION

Problems to be Solved by the Invention

Arctigenin is a stable component, and has high advantageous effects. However, a substance having higher advantageous effects has been desired. An objective of the present invention is to find out a substance having a strong anti-inflammatory effect, a skin-whitening effect, or a skin-elasticity-recovering effect, and provide an anti-aging agent containing such a substance.

Means for Solving the Problems

In order to solve the above-mentioned problems, the present inventors have repeated eager investigations to find out that an arctigenin derivative has an excellent anti-aging effect. Thus, the present invention has been accomplished.

The present invention relates to a preparation for external use to skin for skin-whitening, comprising an arctigenin derivative represented by the following formula:

[Formula 1]

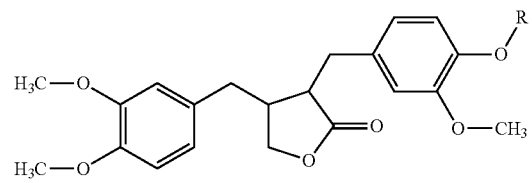

wherein R represents a $C_1$ to $C_{15}$ alkyl, a $C_1$ to $C_{14}$ alkyl-carbonyl, or a hydroxy($C_1$ to $C_{15}$)alkyl.

The present invention also relates to a preparation for external use to skin for recovering skin-elasticity, comprising an arctigenin derivative represented by the formula.

The present invention also relates to an elastase inhibitor, comprising an arctigenin derivative represented by the formula.

The present invention also relates to an endothelin-1 production inhibitor, comprising an arctigenin derivative represented by the formula.

The present invention also relates to an anti-inflammatory agent, comprising an arctigenin derivative represented by the formula.

The present invention also relates to an anti-aging agent, comprising an arctigenin derivative represented by the formula.

The present invention also relates to a tyrosinase inhibitor, comprising an arctigenin derivative represented by the formula.

The present invention also relates to an arctigenin derivative, represented by the following formula:

[Formula 2]

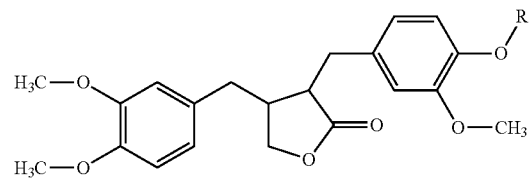

wherein R represents a $C_7$ to $C_{15}$ alkyl, a $C_6$ to $C_{14}$ alkyl-carbonyl, or a hydroxy($C_1$ to $C_{15}$)alkyl.

Effects of the Invention

According to the present invention, provided are an anti-aging agent, an elastase inhibitor, an endothelin-1 production inhibitor, a tyrosinase inhibitor and an anti-inflammatory agent that each contain an arctigenin derivative as an active ingredient. Furthermore, provided are a preparation for external use to skin for anti-inflammation, a preparation for external use to skin for skin-whitening, and a preparation for external use to skin for skin-elasticity recovery each containing the arctigenin derivative.

MODE FOR CARRYING OUT THE INVENTION

Figure 1:
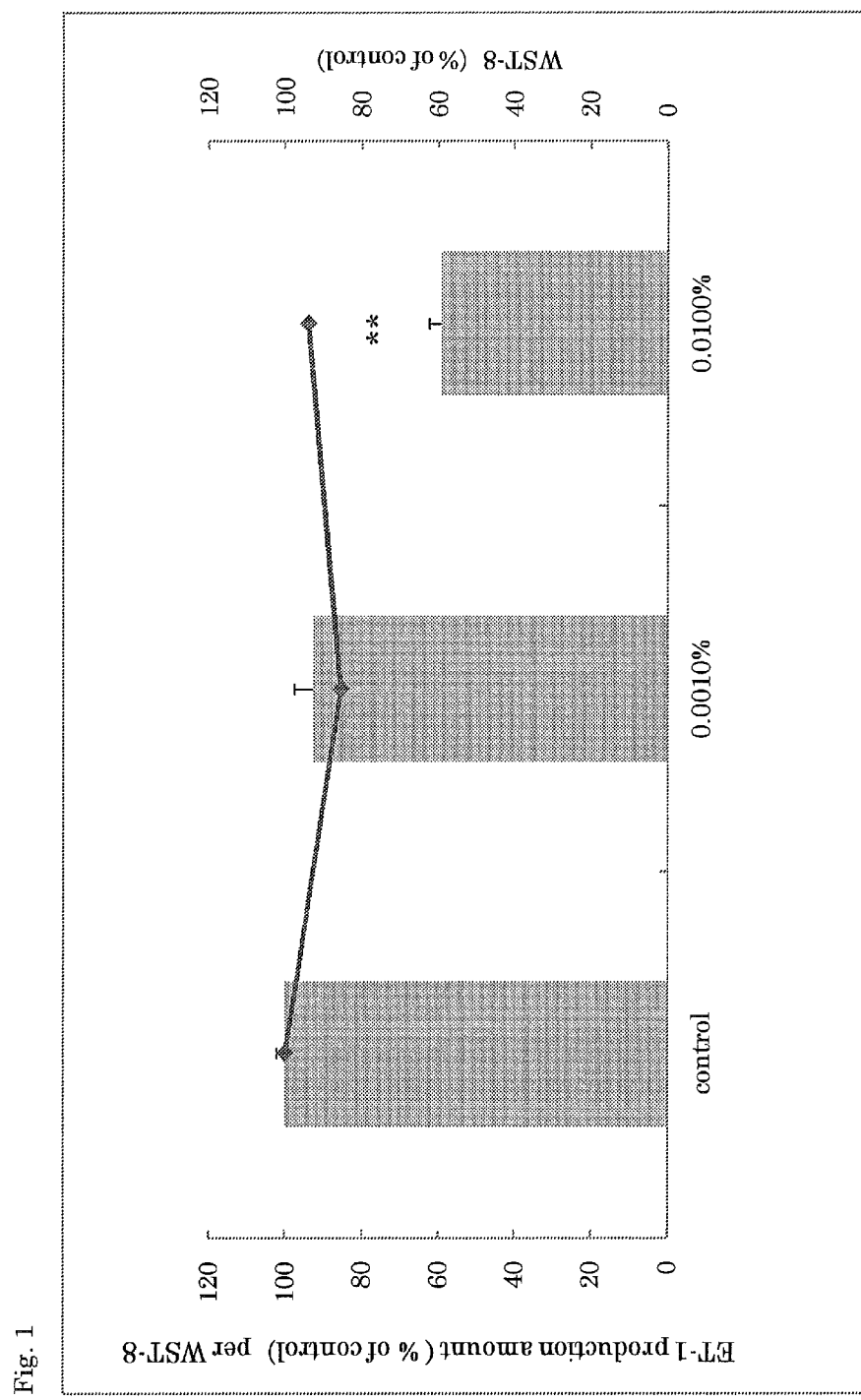
FIG. 1 is a graph showing an endothelin-1 production inhibitory effect of hydroxyethoxyarctigenin.

In the present specification, an arctigenin derivative denotes any compound represented by the following formula:

[Formula 3]

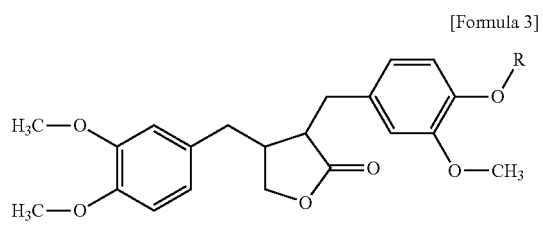

wherein R represents a $C_1$ to $C_{15}$ alkyl, a $C_1$ to $C_{14}$ alkylcarbonyl, or a hydroxy($C_1$ to $C_{15}$)alkyl.

The $C_1$ to $C_{15}$ alkyl denotes any alkyl group having 1 to 15 carbon atoms. The $C_1$ to $C_{14}$ alkylcarbonyl denotes any acyl group in which a carbonyl group is bonded to an alkyl group having 1 to 14 carbon atoms. The whole of the acyl group has 2 to 15 carbon atoms. These alkyls may each be linear or branched.

In the specification, a $C_7$ to $C_{15}$ alkyl denotes any alkyl group having 7 to 15 carbon atoms. A $C_6$ to $C_{14}$ alkylcarbonyl denotes any acyl group in which a carbonyl group is bonded to an alkyl group having 6 to 14 carbon atoms. The whole of this acyl group has 7 to 15 carbon atoms. These alkyls may each be linear or branched.

Among $C_1$ to $C_{14}$ alkylcarbonyls, particularly preferred in the present invention are acetyl, propionyl, butyryl, pivaloyl, valeryl, hexanoyl, heptanoyl, and octanoyl. However, the $C_1$ to $C_{14}$ alkylcarbonyl usable in the present invention is not limited to these groups.

The hydroxy($C_1$ to $C_{15}$)alkyl denotes any group in which an alkyl group having 1 to 15 carbon atoms is bonded to a hydroxyl group. The alkyl may be linear or branched. Particularly preferred are hydroxymethyl and hydroxyethyl. However, the hydroxy($C_1$ to $C_{15}$)alkyl is not limited thereto.

Such a compound is obtainable by modifying appropriately the moiety of the hydroxyl group of arctigenin having the following structural formula:

[Formula 4]

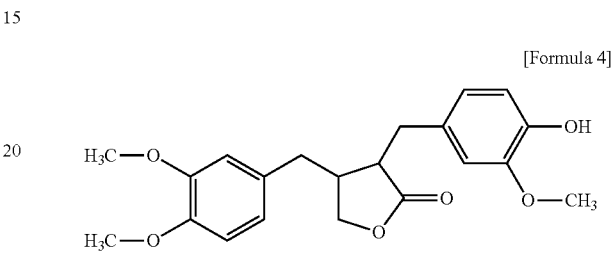

Specifically, an alkylated compound of arctigenin is obtainable by causing a halogenated alkyl to react with the moiety of the hydroxyl group of arctigenin.

A solvent used for the reaction may be an inactive solvent, examples thereof including ketones such as acetone, methyl isobutyl ketone and cyclohexanone, and amides such as dimethylformamide and dimethylacetamide.

At the time of this reaction, it is preferred to cause a base, such as potassium carbonate, sodium hydroxide or potassium hydroxide, to be present.

Specifically, an acid ester of arctigenin is obtainable by causing an organic acid to undergo condensation reaction with the moiety of the hydroxyl group of arctigenin.

A solvent used for the reaction is preferably, for example, an aromatic hydrocarbon such as benzene, toluene or xylene, or a halogenated hydrocarbon such as dichloromethane, chloroform or carbon tetrachloride. However, the solvent is not limited thereto.

A hydroxy($C_1$ to $C_{15}$)alkylated compound of arctigenin is obtainable by causing a halogenated alcohol to react with the moiety of the hydroxyl group of arctigenin.

A solvent used for the reaction may be an inactive solvent, examples thereof including ketones such as acetone, methyl isobutyl ketone and cyclohexanone, and amides such as dimethylformamide and dimethylacetamide.

At the time of this reaction, it is preferred to cause a base, such as potassium carbonate, sodium hydroxide or potassium hydroxide, to be present.

The resultant compound is appropriately purified to be used as an active ingredient of a medicine. The method for the purification is not particularly limited, and may be a conventional separating means or method, such as a fractional crystallization method, a purifying method using chromatography, a solvent extraction method, or a solid-phase extraction method. Using the method, the appropriate isolation or purification can be attained.

In the present invention, the term "anti-aging agent" denotes any preparation for external use to skin or any different-form medicine for preventing or slowing down an aging phenomenon, typical examples thereof including an inflammation, and a skin deterioration or roughness as well as skin wrinkles, skin sagging, skin dullness, skin spots, and dark circles under eyes. More specifically, the agent denotes a medicine against one or more out of various skin-aging phenomena, examples of the medicine including a medicine for skin-whitening, a medicine for anti-wrinkle effect or any other skin-elasticity-recovering effect, and a medicine for anti-inflammation.

For maintaining the elasticity of the skin, the presence of a substance named elastin plays an important role. It has been known that wrinkles or sagging is promoted by the action of elastase for decomposing elastin. It is therefore effective for anti-wrinkle or any other skin-elasticity-recovering effect to obtain a substance for inhibiting the activity of elastase.

Melanin, which is related particularly to the skin dullness, liver spots and dark circles under eyes, is a factor for establishing the color of a skin, and causes the skin dullness, liver spots or dark circles under eyes. In other words, the color of a skin is determined depending on the amount and the nature of melanin, and the degree of the distribution thereof. Accordingly, the inhibition of the production of melanin results in the exhibition of a skin-whitening effect.

Endothelin-1 is secreted from keratinocytes when a person is irradiated with ultraviolet rays and is known as a substance for promoting the synthesis of melanin. Consequently, the inhibition of the production of endothelin-1 causes the inhibition of the synthesis of melanin to result in a skin-whitening effect. It is also known that the production of endothelin-1 causes an inflammatory reaction. Thus, the inhibition of the production of endothelin-1 is useful for relieving an inflammatory reaction. Furthermore, it is known that endothelin-1 is related to cardiovascular diseases.

Tyrosinase is an oxidase, which melanocytes have, for creating melanin pigment. In order to prevent or treat a pigmentation associated with skin spots, skin dullness, dark circles under eyes or other drawbacks of skin against stimulation by ultraviolet rays or others, the activity of tyrosinase, which is a melanin synthesizing enzyme, can be inhibited.

In the present invention, the arctigenin derivative includes, in the category thereof, salts of any arctigenin derivative. The salts of the arctigenin derivative are, for example, alkali metal salts thereof, alkaline earth metal salts thereof, or salts thereof with any organic base. Examples of the salts include respective salts thereof with sodium, potassium, calcium, magnesium, ammonium, diethanolamine, and ethylenediamine. These salts are each obtainable, for example, by converting a sulfonate group or carboxyl group present in an arctigenin derivative or the like into a salt in a known manner. Other examples of the salts include respective salts thereof with ammonia, methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, L-glucamine, and other amines; and respective salts thereof with lysine, δ-hydroxylysine, arginine, and other basic amino acids. Additional examples of the salts include respective salts thereof with hydrochloric acid, hydrobromic acid, sulfuric acid, nitric acid, phosphoric acid, and other mineral acids; respective salts thereof with methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, salicylic acid, and other organic acids; and respective salts thereof with aspartic acid, glutamic acid and other acidic amino acids.

Alternatively, the arctigenin derivative of the present invention may include, in the category thereof, solvates and hydrates of salts thereof.

The medicine or preparation for external use to skin containing, as an active ingredient, the arctigenin derivative of the present invention may be supplied in a widely usable form of any pharmaceutical preparation or composition as a pharmaceutical product, a quasi-pharmaceutical product, a food, a cosmetic product or any other product; and is preferably supplied in the form of a pharmaceutical preparation or composition usable as a cosmetic product.

When the composition containing the arctigenin derivative of the present invention is made into a form of any one of a pharmaceutical product, a quasi-pharmaceutical product, a food and a cosmetic product, the content by percentage of the arctigenin derivative is preferably 0.00001% or more and 50% by weight or less, more preferably 0.00001% or more and 20% by weight or less, even more preferably 0.001% or more and 5% by weight or less.

About the dosage of the arctigenin derivative when the present invention is used for a pharmaceutical product or a food such as a health food, the daily dry-weight thereof per adult may be adjusted into the range of about 0.0001 to 10 g/kg, more preferably 0.0001 to 2 g/kg.

Form for Internal Use

The arctigenin derivative, which is an active ingredient for the present invention, may be blended into a pharmaceutically allowable carrier, and then orally or parenterally administered in the form of a solid pharmaceutical preparation such as a tablet, capsule, granule, or powdered drug, or a liquid pharmaceutical preparation such as a syrup agent or parenteral injection. Further examples of the form thereof include a suppository, patch, inhalant, drop, percutaneously absorbing agent, and transmucosal absorbing agent. These pharmaceutical preparations may each contain ordinary additives. The pharmaceutically allowable carrier may be an organic or inorganic carrier that is conventionally usable as a pharmaceutical preparing raw-material and may be of various types. The carrier is blended in the form of, for example, an excipient, lubricant, binder, or disintegrating agent in a solid pharmaceutical preparation; or a solvent, dissolution aid, suspending agent, isotonizing agent, buffer or soothing agent in a liquid pharmaceutical preparation. If necessary, a preservative, anti-oxidant, colorant or sweetening agent, or any other pharmaceutical preparing admixture is usable.

Preferred examples of the excipient include sugar alcohols such as D-sorbitol, mannitol and xylitol, saccharides such as glucose, sucrose, lactose and fructose, crystalline cellulose, sodium carmellose, sodium croscarmellose, calcium hydrogen phosphate, wheat starch, rice starch, corn starch, potato starch, dextrin, β-cyclodextrin, light silicic anhydride, titanium oxide, magnesium metasilicate aluminate, talc, and kaolin.

Preferred examples of the binder include cellulose derivatives such as methylcellulose, ethylcellulose, hydroxypropylcellulose and hydroxypropylmethylcellulose, polyvinyl pyrrolidone, polyvinyl alcohol, acrylic acid type polymers, gelatin, gum arabic, pullulan, α-starch, agar, gum tragacanth, sodium alginate, and a propylene glycol ester of alginic acid.

Preferred examples of the disintegrating agent include starch, low-substitution-degree hydroxypropylcellulose, potassium carboxymethylcellulose, sodium croscarmellose, hydroxypropyl starch, and partially α-modified starch. Preferred examples of the solvent include water for injection, alcohols, propylene glycol, macrogol, sesame oil, and corn oil.

Preferred examples of the lubricant include stearic acid, magnesium stearate, calcium stearate, polyoxylstearate, cetanol, talc, hardened oil, saccharose fatty acid esters, dimethylpolysiloxane, beeswax, and bleached beeswax.

Preferred examples of the dissolution aid include polyethylene glycol, propylene glycol, D-mannitol, benzyl benzoate, ethanol, trisaminomethane, cholesterol, triethanolamine, sodium carbonate, and sodium citrate. Preferred examples of the suspending agent include surfactants such as stearyltriethanolamine, sodium laurylsulfonate, laurylaminopropionic acid, lecithin, benzalkonium chloride, benzethonium chloride, and glycerin monostearate; and hydrophilic polymers such as polyvinyl alcohol, polyvinyl pyrrolidone, sodium carboxymethylcellulose, methylcellulose, hydroxymethylcellulose, hydroxyethylcellulose, and hydroxypropylcellulose.

Preferred examples of the isotonizing agent include sodium chloride, glycerin, and D-mannitol. Preferred examples of the buffer include phosphates, acetates, carbonates, citrates and other buffers. Preferred examples of the soothing agent include benzyl alcohol. Preferred examples of the preservative include p-oxybenzoates, chlorobutanol, benzyl alcohol, phenethyl alcohol, dehydroacetic acid, and sorbic acid. Preferred examples of the anti-oxidant include sulfites, and ascorbic acid.

When a medicine containing the arctigenin derivative of the present invention is made into a solid pharmaceutical preparation, the method for producing this pharmaceutical preparation is not particularly limited as far as the method includes the step of mixing the arctigenin derivative with a pharmaceutical preparing raw-material to produce the solid pharmaceutical preparation. The method may be a method known in the prior art.

The method is, for example, a method of kneading a pharmaceutical preparation composition containing the arctigenin derivative and a pharmaceutical preparing raw-material, and passing the composition through a screen to be shaped into an extruded and granulated product, crushing the product, and adjusting the resultant grains; a method of adding kneading-water to the same pharmaceutical preparation composition, stirring and granulating the composition through a vertical granulator so as to be shaped, and then using a Comil to crush and pass the resultant grains through a sieve; a method of using a roller compactor to compress the same pharmaceutical preparation composition, and using a roll granulator to crush and pass the resultant compressed composition through a sieve; or a method of stirring and granulating the same composition, and then drying the resultant on a fluidized bed.

When the solid pharmaceutical preparation is produced by, for example, direct tableting, it is advisable to mix a pharmaceutical preparation composition containing the arctigenin derivative and a pharmaceutical preparing raw-material with each other, and then directly put the mixture into a tableting machine to attain the tableting.

Preparation Form for External Use to Skin

A medicine or preparation for external use to skin containing the arctigenin derivative of the present invention as an active ingredient is usable in the form of a pharmaceutical product, a quasi-pharmaceutical product, a preparation for external use to skin or a cosmetic product. As to such an external preparation form, the arctigenin derivative is mixed with a known base or carrier to be added in an external application agent (cosmetic product, quasi-pharmaceutical product or pharmaceutical product), so as to be made into a composition as far as the advantageous effects of the present invention are not damaged. Additionally, for example, the following may be blended into such an external application agent: a surfactant, oil, alcohol, humectant, thickener, preservative, anti-oxidant, chelating agent, pH adjustor, stabilizer, dispersing agent, perfume, colorant, dye or pigment, pearl gloss supplier, blood circulation promoter, moisturizing agent, ultraviolet absorbent, ultraviolet scattering component, cleaning agent, anti-bacterial agent, astringent component, vitamin, amino acid, keratin softening component, cell activating component, and water. The additives are usable alone or in any combination of two or more thereof.

As to a medicine or preparation for external use to skin containing the arctigenin derivative of the present invention as an active ingredient, examples of a known form of a pharmaceutical product, cosmetic product or quasi-pharmaceutical product thereof include a liquid medicine, suspension, emulsion, creamy agent, ointment, gel, liniment, lotion, aerosol, powder, poultice, sheet agent in which a nonwoven fabric is impregnated with a pharmaceutical liquid, and stick agent such as a lipstick. The medicine or preparation for external use to skin is used in particular preferably in the form of a liquid medicine, suspension, emulsion, creamy agent, ointment, gel, lotion or gel. By making the medicine or preparation for external use to skin into such a form, the anti-aging effect according to the present invention can be sufficiently exhibited.

More specific examples of the form of the cosmetic product composition include basic cosmetic products for anti-inflammation, skin-whitening, or skin-elasticity-recovery effects (examples thereof including anti-wrinkle effect), such as a cleansing agent, facial cleansing agent, face lotion, milky lotion, cream, liquid cosmetic product, facial mask, and lip cream therefor; makeup cosmetic products for anti-inflammation, skin-whitening, or skin-elasticity-recovery effects (examples thereof including anti-wrinkle effect), such as a foundation, cosmetic base, lip cream, lip stick, and cheek colorant therefor; cosmetic products for a scalp/hair for anti-inflammation, or skin-elasticity-recovery effects (examples thereof including anti-wrinkle effect), such as a shampoo, conditioner, or hairspray therefor, hair growth tonics; body washing agents for anti-inflammation, skin-whitening, or skin-elasticity-recovery effects (examples thereof including anti-wrinkle effect); and body cosmetic products, such as bath additives.

<Base or Carrier>

Examples of the base or carrier include hydrocarbons such as liquid paraffin, squalane, gelatinized hydrocarbons (such as plastibase), ozocerite, α-olefin oligomers, and light liquid paraffin; silicone oils such as methylpolysiloxane, crosslinked methylpolysiloxane, highly polymerized methylpolysiloxane, cyclic silicone, alkyl-modified silicone, crosslinked alkyl-modified silicone, amino-modified silicone, polyether-modified silicon, polyglycerin-modified silicone, crosslinked polyether-modified silicone, crosslinked alkylpolyether-modified silicone, silicone/alkyl-chain co-modified polyether-modified silicone, silicone/alkyl-chain co-modified polyglycerin-modified silicone, polyether-modified branched silicone, polyglycerin-modified branched silicone, acrylsilicone, phenyl-modified silicone, and silicone resin; cellulose derivatives such as ethylcellulose, hydroxypropylcellulose, and hydroxypropylmethylcellulose; polyvinyl pyrrolidone; carrageenan; polyvinyl butyrate; polyethylene glycol; dioxane; butylene glycol polyadipate; esters such as isopropyl myristate, octyldodecyl myristate, isopropyl palmitate, cetyl palmitate, isononyl isononanoate, and pentaerythritol tetra (2-ethylhexanoate); polysaccharides such as dextrin and maltodextrin; lower alcohols such as ethanol, and isopropanol; glycol ethers such as ethylene glycol monomethyl ether, ethylene glycol monoethyl ether, ethylene glycol monopropyl ether, diethylene glycol monomethyl ether, diethylene glycol monoethyl ether, diethylene glycol monopropyl ether, diethylene glycol monobutyl ether, propylene glycol monoethyl ether, propylene glycol monopropyl ether, dipropylene glycol monoethyl ether, and dipropylene glycol monopropyl ether; polyhydric alcohols such as polyethylene glycol, propylene glycol, 1,3-butylene glycol, glycerin, and isoprene glycol; water, and other aqueous bases.

These bases and carriers are usable alone or in any combination of two or more thereof.

Examples of the anti-oxidant include dibutylhydroxytoluene, butylhydroxyanisole, sorbic acid, sodium sulfite, ascorbic acid, erythorbic acid, and L-cysteine hydrochloride.

Examples of the surfactant include sorbitan fatty acid esters, such as sorbitan monoisostearate, sorbitan monolaurate, sorbitan monopalmitate, sorbitan monostearate, diglycerol sorbitan penta-2-ethylhexylate, and diglycerol sorbitan tetra-2-ethylhexylate; fatty acid esters of propylene glycol, such as propylene glycol monostearate; hardened castor oils, such as polyoxyethylene hydrogenated castor oil 40 (HCO-40), polyoxyethylene hydrogenated castor oil 50 (HCO-50), polyoxyethylene hydrogenated castor oil 60 (HCO-60), and polyoxyethylene hydrogenated castor oil 80; polyoxyethylene sorbitan fatty acid esters, such as polyoxyethylene (20) sorbitan monolaurate (polysorbate 20), polyoxyethylene (20) sorbitan monostearate (polysorbate 60), polyoxyethylene (20) sorbitan monooleate (polysorbate 80), and polyoxyethylene (20) sorbitan isostearate; fatty acid glyceryl of polyoxyethylene monococonut oil; glycerin alkyl ethers; alkyl glucoside; polyoxyalkylene alkyl ethers, such as polyoxyethylene cetyl ether; amines such as stearylamine, and oleylamine; silicone surfactants such as polyoxyethylene/methylpolysiloxane copolymer, lauryl PEG-9 polydimethylsiloxyethyldimethicone, and PEG-9 polydimethylsiloxyethyldimethicone; anionic surfactants such as lauric acid salts, palmitic acid salts, cocoylglutamic acid salts, coconut oil methylalanine salts, acylmethyltaurine salts, and polyoxyethylene laurylsulfate; and amphoteric surfactants such as lauryldiaminoethyl glycine salts, and coconut oil fatty acid betaine salts.

Examples of the thickener include guar gum, locust bean gum, carrageenan, xanthan gum, carboxymethylcellulose, hydroxymethylcellulose, hydroxyethylcellulose, hydroxypropyl cellulose, hydroxypropylmethylcellulose, polyvinyl alcohol, polyvinyl pyrrolidone, carboxyvinyl polymer, alkyl acrylate and methacrylate copolymer, polyethylene glycol, bentonite, (Na hydroxyethyl acrylate/acryloyldimethyl taurine) copolymer, and (ammonium acryloyldimethyltaurine/vinyl pyrrolidone) copolymer.

Examples of the preservative include benzoic acid, sodium benzoate, dehydroacetic acid, sodium dehydroacetate, isobutyl p-oxybenzoate, isopropyl p-oxybenzoate, butyl p-oxybenzoate, ethyl p-oxybenzoate, propyl p-oxybenzoate, benzyl p-oxybenzoate, methyl p-oxybenzoate, and phenoxyethanol.

Examples of the pH adjuster include inorganic acids (such as hydrochloric acid and sulfuric acid), and organic acids (such as lactic acid, sodium lactate, citric acid, sodium citrate, succinic acid, and sodium succinate), inorganic bases (such as potassium hydroxide, and sodium hydroxide), and organic bases (such as triethanolamine, diisopropanolamine, and triisopropanolamine).

Examples of the chelating agent include a disodium salt of EDTA, and a calcium disodium salt of EDTA.

Examples of the stabilizer include sodium polyacrylate, and dibutylhydroxytoluene, and butylhydroxyanisole.

The additives are usable alone or in any combination of two or more thereof.

<Other Active Ingredients>

The external preparation composition of the present invention may contain some other active ingredient as far as the advantageous effects of the present invention are not damaged. Specific examples of the active ingredient include a moisturizing agent, an anti-bacterial component, a vitamin, a peptide or any derivative thereof, an amino acid or any derivative thereof, a cell activating component, and a blood circulation promoter.

Examples of the moisturizing agent include polyhydric alcohols such as glycerin, 1,3-butylene glycol, propylene glycol, polyethylene glycol, and diglycerin; saccharides such as trehalose, xylitol, and oligosaccharide; polymeric compounds such as sodium hyaluronate, heparin analogue substances, sodium chondroitin sulfate, collagen, elastin, keratin, chitin, and chitosan; amino acids such as glycine, aspartic acid, and arginine; natural moisturizing factors such as sodium lactate, urea, and sodium pyrrolidonecarboxylate; lipids such as ceramide, cholesterol, and phospholipid; and plant extracts such as camomile extract, hamamelis extract, tea extract and perilla extract.

Examples of the vitamin include vitamin E group compounds, such as dl-α-tocopherol, dl-α-tocopherol acetate, dl-α-tocopherol succinate, and dl-α-tocopherol calcium succinate; vitamin B2 group compounds such as riboflavin, flavin mononucleotide, flavin adenine dinucleotide, riboflavin butyrate, riboflavin tetrabutyrate, sodium riboflavin 5'-phosphate, and tetranicotinate riboflavin; nicotinic acid group compounds such as dl-α-tocopherol nicotinate, benzyl nicotinate, methyl nicotinate, β-butoxyethyl nicotinate, and 1-(4-methylphenyl)ethyl nicotinate; vitamin C group compounds such as ascorbigen-A, ascorbyl stearate, ascorbyl palmitate, and L-ascorbyl dipalmitate; vitamin D group compounds such as methylhesperidin, ergocalciferol, and cholecalciferol; vitamin K group compounds such as phylloquinone and farnoquinone, γ-orizanol, dibenzoylthiamine, and dibenzoylthiamine hydrochloride; vitamin B1 group compounds such as thiamine hydrochloride, thiaminecetyl hydrochloride, thiamine thiocyanate, thiaminelauryl hydrochloride, thiamine nitrate, thiamine monophosphate, thiamine lysine salt, thiamine triphosphate, thiamine monophosphoester phosphate, thiamine monophosphoester, thiamine diphosphoester, thiamine diphosphoester hydrochloride, thiamine triphosphoester, and thiamine triphosphoester monophosphate; vitamin B6 group compounds such as pyridoxine hydrochloride, pyridoxine acetate, pyridoxal hydrochloride, pyridoxal-5'-phosphate, and pyridoxamine hydrochloride; vitamin B12 compounds such as cyanocobalamine, hydroxocobalamine, and deoxyadenosylcobalamine; folic acid group compounds such as folic acid, and pteroylglutamic acid; nicotinic acid group compounds such as nicotinic acid, and nicotinamide; pantothenic acid group compounds such as pantothenic acid, calcium pantothenate, pantothenyl alcohol (panthenol), D-pantecine, D-pantethine, coenzyme A, and pantothenyl ethyl ether; biotin group compounds such as biotin, and bioticine; vitamin C group compounds such as ascorbic acid, sodium ascorbate, dehydroascorbic acid, ascorbic acid phosphoester sodium, ascorbic acid phosphoester magnesium, and other ascorbic acid derivatives; and vitamin-like effectors such as carnitine, ferulic acid, α-lipoic acid, and orotic acid.

Examples of the peptide or any derivative thereof include keratin-decomposed peptide, hydrolyzed keratin, collagen, fish-derived collagen, atelocollagen, gelatin, elastin, elastin-decomposed peptide, collagen-decomposed peptide, hydrolyzed collagen, hydroxypropylammonium chloride hydrolyzed collagen, elastin-decomposed peptide, conchiolin-decomposed peptide, hydrolyzed conchiolin, silk-protein-decomposed peptide, hydrolyzed silk, sodium lauroyl hydrolyzed silk, soybean-protein-decomposed peptide, hydrolyzed soybean protein, wheat protein, wheat-protein-decomposed peptide, hydrolyzed wheat protein, casein-decomposed peptide, and acylated peptides (such as palmitoyl oligopeptide, palmitoylpentapeptide, and palmitoyltetrapeptide).

Examples of the amino acid or any derivative thereof include betaine (trimethylglycine), proline, hydroxyproline, arginine, lysine, serine, glycine, alanine, phenylalanine, β-alanine, threonine, glutamic acid, glutamine, asparagine, aspartic acid, cysteine, cystine, methionine, leucine, isoleucine, valine, histidine, taurine, γ-aminobutyric acid, γ-amino-β-hydroxybutyric acid, carnitine, carnosine, and creatine.

Food

The anti-aging agent, endothelin-1 production inhibitor, or elastase inhibitor of the present invention, which contains an arctigenin derivative, may be supplied in the state of being incorporated into a food or functional food. Examples of the food or functional food include cooked rice; various noodles such as buckwheat noodles, wheat noodles, bean-starch vermicelli, Chinese noodles, instant noodles, and cup noodles; drinks such as a refreshing drink, a carbonated drink, an energy drink, a fruit drink, a lactic acid beverage, and a sports beverage; curry roux, stew, and various kinds of soups; ice confectioneries such as ice cream, sherbet, snow cone (shaved ice); confectioneries such as a toffee, a cookie, a candy, chewing gum, a chocolate, a tablet confectionery, snack food, a biscuit, jelly, jam, cream, and other baked sweets; processed sea foods and processed animal-derived foods such as a kamaboko (fish minced and steamed), a pounded fish cake (hanpen called in Japanese), ham and sausage; milk products such as processed milk and fermented milk; oils and fats, and oil-and-fat processed foods such as salad oil, tempura oil, margarine, mayonnaise, shortening, whipped cream and dressing; seasonings such as sauce, dressing, miso, soy sauce, and soy-based sauce; soup, stew, salad, precooked food, rice seasoning, and salted vegetables; and healthy/nutritional supplementary foods in various forms.

Furthermore, it is allowable to prepare supplements (such as a powdered medicine, granulated powdered medicine, soft capsule, hard capsule, tablet, chewable medicine, fast-disintegrating tablet, syrup, and liquid medicine) containing the arctigenin derivative of the present invention.

The arctigenin derivative of the present invention may be incorporated into baits or feeds for animals, such as pets.

Additives are added to the foods if necessary. Examples of the additives include glucose, fructose, saccharose, maltose, sorbitol, stevioside, rubusoside, corn syrup, lactose, mannite, dextrin, citric acid, sodium citrate, tartaric acid, malic acid, succinic acid, lactic acid, L-ascorbic acid, dl-α-tocopherol, sodium erythorbate, glycerin, propylene glycol, glycerin fatty acid esters (glycerin esters of fatty acids), polyglycerin fatty acid esters, saccharose fatty acid esters, sorbitan fatty acid esters, gum arabic, carrageenan, casein, gelatin, pectin, agar, vitamin C, vitamin B group compounds, vitamin E, nicotinamide, calcium pantothenate, amino acids, calcium salts, surfactants, colorants, perfumes, and preservatives.

When a medicine containing the arctigenin derivative is used for pharmaceuticals, the medicine may be used in the form of a kit. This form is specifically in such a form that constituent-components which constitute a pharmaceutical composition and are different from each other are beforehand wrapped into different containers or packs, respectively, and these components are mixed with each other just before used. Examples of the containers include sealable ampules, test tubes, vials, flasks, bottles, and syringes; and analogues thereof.

Furthermore, the present invention relates to use of an arctigenin derivative represented by the following formula:

[Formula 5]

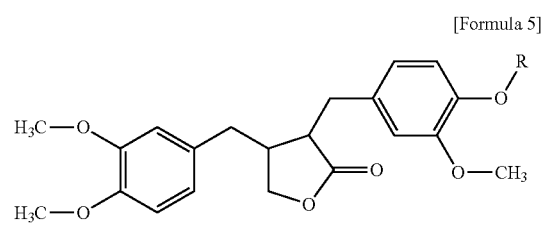

wherein R represents a $C_1$ to $C_{15}$ alkyl, a $C_1$ to $C_{14}$ alkyl-carbonyl, or a hydroxy($C_1$ to $C_{15}$)alkyl for producing an elastase inhibitor.

The present invention also relates to use of an arctigenin derivative represented by the following formula:

[Formula 6]

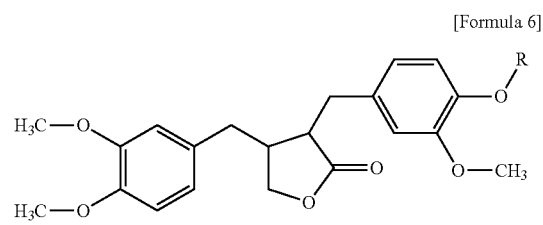

wherein R represents a $C_1$ to $C_{15}$ alkyl, a $C_1$ to $C_{14}$ alkyl-carbonyl, or a hydroxy($C_1$ to $C_{15}$)alkyl for producing an endothelin-1 production inhibitor.

The present invention also relates to use of an arctigenin derivative represented by the following formula:

[Formula 7]

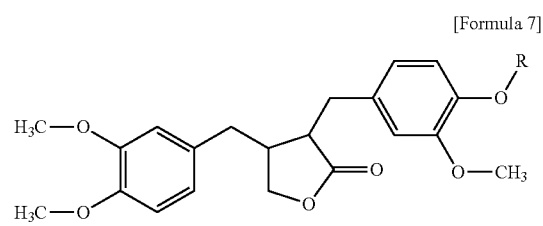

wherein R represents a $C_1$ to $C_{15}$ alkyl, a $C_1$ to $C_{14}$ alkyl-carbonyl, or a hydroxy($C_1$ to $C_{15}$)alkyl for producing an anti-inflammatory agent.

The present invention also relates to use of an arctigenin derivative represented by the following formula:

[Formula 8]

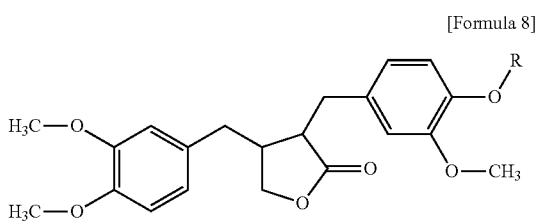

wherein R represents a $C_1$ to $C_{15}$ alkyl, a $C_1$ to $C_{14}$ alkylcarbonyl, or a hydroxy($C_1$ to $C_{15}$)alkyl for producing an anti-aging agent.

The present invention also relates to use of an arctigenin derivative represented by the following formula:

[Formula 9]

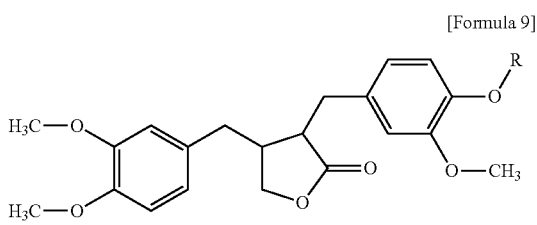

wherein R represents a $C_1$ to $C_{15}$ alkyl, a $C_1$ to $C_{14}$ alkylcarbonyl, or a hydroxy($C_1$ to $C_{15}$)alkyl for producing a tyrosinase inhibitor.

EXAMPLES

The following will describe the present invention specifically byway of test examples, working examples thereof, and others. However, the present invention is not limited to the working examples.

Example 1

Synthesis of Acetoxyarctigenin

The following were mixed with each other: 0.5 mL (5 mol) of acetic anhydride, and 0.5 mL (6 mol) of pyridine. Thereto was added 1 g (2.7 mmol) of arctigenin, and then the reactive components were caused to react with each other at room temperature for 3 hours. The reaction liquid was poured into 100 mL of ice water, and the resultant was stirred. The precipitated crystal was collected by filtration to yield 834.5 mg (yield: 74.6%) of acetoxyarctigenin.

Mass analysis: ESI-MS/MS, m/z; 415.6 (M+H)$^+$
Molecular formula: $C_{23}H_{26}O_7$
In a $^1$H-NMR spectrum thereof, main chemical shift peaks relative to CDCl$_3$ (standard substance) are as follows:
6.93 (d, 1H), 6.75 (d, 2H), 6.66 (dd, 1H), 6.54 (dd, 1H), 6.50 (d, 1H), 4.17 (dd, 1H), 3.90 (t, 1H), 3.85 (s, 3H), 3.82 (s, 3H), 3.77 (S, 3H), 2.94 (d, 2H), 2.49-2.68 (m, 4H), 2.30 (S, 3H)

Example 2

Synthesis of Arctigenin Propionate

Into 10 mL of chloroform were dissolved 75 mg (0.2 mmol) of arctigenin and 14.8 mg (0.2 mmol) of propionic acid. Thereto were added 76.68 mg (0.4 mmol) of a water-soluble carbodiimide, (1-ethyl-3-(3-dimethylaminopropyl)-carbodiimide hydrochloride (trade name: WSCD.HCl; manufacturer's name: Peptide Institute, Inc.) and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of NaHCO$_3$ in water. The chloroform layer was distilled off under a reduced pressure to yield 58.3 mg (yield: 67.8%) of arctigenin propionate.

Mass analysis: ESI-MS/MS, m/z; 429.2 (M+H)$^+$
Molecular formula: $C_{24}H_{28}O_7$
6.93 (d, 1H), 6.76 (d, 1H), 6.74 (d, 1H), 6.56 (dd, 1H), 6.53 (dd, 1H), 6.50 (d, 1H), 4.17 (dd, 1H), 3.90 (t, 1H), 3.85 (s, 3H), 3.82 (s, 3H), 3.75 (S, 3H), 2.97 (m, 2H), 2.54-2.64 (m, 6H), 1.26 (t, 3H)

Example 3

Arctigenin Butanoate

Into 10 mL of chloroform were dissolved 75 mg (0.2 mmol) of arctigenin and 17.6 mg (0.2 mmol) of butanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of NaHCO$_3$ in water. The chloroform layer was distilled off under a reduced pressure to yield arctigenin butanoate.

Example 4

Arctigenin Pentanoate

Into 10 mL of chloroform were dissolved 75 mg (0.2 mmol) of arctigenin and 20.4 mg (0.2 mmol) of pentanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of NaHCO$_3$ in water. The chloroform layer was distilled off under a reduced pressure to yield arctigenin pentanoate.

Example 5

Arctigenin Hexanoate

Into 10 mL of chloroform were dissolved 75 mg (0.2 mmol) of arctigenin and 23.2 mg (0.2 mmol) of hexanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of NaHCO$_3$ in water. The chloroform layer was distilled off under a reduced pressure to yield arctigenin hexanoate.

Molecular formula: $C_{27}H_{34}O_7$
6.92 (d, 1H), 6.76 (d, 1H), 6.74 (d, 1H), 6.67 (dd, 1H), 6.54 (dd, 1H), 6.49 (d, 1H), 4.17 (dd, 1H), 3.90 (dd, 1H), 3.85 (s, 3H), 3.82 (s, 3H), 3.75 (S, 3H), 2.97 (m, 2H), 2.55-2.58 (m, 6H), 1.75 (q, 2H), 1.38 (m, 4H), 0.92 (t, 3H)

Example 6

Arctigenin Heptanoate

Into 10 mL of chloroform were dissolved 75 mg (0.2 mmol) of arctigenin and 26.0 mg (0.2 mmol) of heptanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield arctigenin heptanoate.

Example 7

Arctigenin Octanoate

Into 10 mL of chloroform were dissolved 75 mg (0.2 mmol) of arctigenin and 28.8 mg (0.2 mmol) of octanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield arctigenin octanoate.

Example 8

Arctigenin Nonanoate

Into 10 mL of chloroform were dissolved 75 mg (0.2 mmol) of arctigenin and 31.6 mg (0.2 mmol) of nonanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield 60.3 mg (yield: 58.7%) of arctigenin nonanoate.

Mass analysis: ESI-MS/MS, m/z; 513.2 $(M+H)^+$
Molecular formula: $C_{30}H_{40}O_7$
6.92 (d, 1H), 6.76 (d, 1H), 6.73 (d, 1H), 6.67 (dd, 1H), 6.53 (dd, 1H), 6.49 (d, 1H), 4.16 (dd, 1H), 3.90 (dd, 1H), 3.85 (s, 3H), 3.82 (s, 3H), 3.75 (S, 3H), 2.97 (m, 2H), 2.54-2.63 (m, 6H), 1.75 (q, 2H), 1.28 (m, 10H), 0.88 (t, 3H)

Example 9

Arctigenin Decanoate

Into 10 mL of chloroform were dissolved 75 mg (0.2 mmol) of arctigenin and 34.5 mg (0.2 mmol) of decanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield arctigenin decanoate.

Example 10

Arctigenin Undecanoate

Into 10 mL of chloroform were dissolved 75 mg (0.2 mmol) of arctigenin and 37.3 mg (0.2 mmol) of undecanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield arctigenin undecanoate.

Example 11

Arctigenin Dodecanoate

Into 10 mL of chloroform were dissolved 75 mg (0.2 mmol) of arctigenin and 40.1 mg (0.2 mmol) of dodecanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield 36.6 mg of arctigenin dodecanoate.

Molecular formula: $C_{33}H_{46}O_7$
6.92 (d, 1H), 6.76 (d, 1H), 6.73 (d, 1H), 6.67 (dd, 1H), 6.54 (dd, 1H), 6.49 (d, 1H), 4.17 (dd, 1H), 3.90 (dd, 1H), 3.85 (s, 3H), 3.82 (s, 3H), 3.75 (S, 3H), 2.97 (m, 2H), 2.55-2.58 (m, 6H), 1.75 (q, 2H), 1.26 (m, 16H), 0.88 (t, 3H)

Example 12

Arctigenin Tridecanoate

Into 10 mL of chloroform were dissolved 75 mg (0.2 mmol) of arctigenin and 42.9 mg (0.2 mmol) of tridecanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of $NaHCO_3$ in water. The chloroform layer was distilled off under a reduced pressure to yield arctigenin tridecanoate.

Example 13

Arctigenin Myristate

Into 10 mL of chloroform were dissolved 75 mg (0.2 mmol) of arctigenin and 45.8 mg (0.2 mmol) of myristic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of NaHCO$_3$ in water. The chloroform layer was distilled off under a reduced pressure to yield arctigenin myristate.

Example 14

Arctigenin Pentadecanoate

Into 10 mL of chloroform were dissolved 75 mg (0.2 mmol) of arctigenin and 48.5 mg (0.2 mmol) of pentadecanoic acid. Thereto were added 76.68 mg (0.4 mmol) of the water-soluble carbodiimide and 48 mg (0.4 mmol) of DMAP. In chloroform, the reactive components were caused to react with each other at room temperature for 6 hours. Water was added to the reaction liquid, and this system was stirred. The resultant organic layer was then washed with 1 N HCl, and a saturated solution of NaHCO$_3$ in water. The chloroform layer was distilled off under a reduced pressure to yield arctigenin pentadecanoate.

Example 15

Hydroxymethoxyarctigenin

Into 2 mL of DMF were dissolved 75 mg (0.2 mmol) of arctigenin and 79.8 mg (1.2 mmol) of 1-chloromethanol. Thereto was further added 165.9 mg (1.2 mmol) of potassium carbonate. In this way, the reactive components were caused to react with each other at 100° C. for 3 hours. The reaction liquid was filtrated, and the resultant filtrate was distilled off under a reduced pressure. Ethyl acetate and water were added to the residue, and this system was stirred. The organic layer was then distilled off under a reduced pressure to yield hydroxymethoxyarctigenin.

Example 16

Hydroxyethoxyarctigenin

Into 2 mL of DMF were dissolved 75 mg (0.2 mmol) of arctigenin and 96.6 mg (1.2 mmol) of 2-chloroethanol. Thereto was further added 165.9 mg (1.2 mmol) of potassium carbonate. In this way, the reactive components were caused to react with each other at 100° C. for 3 hours. The reaction liquid was filtrated, and the resultant filtrate was distilled off under a reduced pressure. Ethyl acetate and water were added to the residue, and this system was stirred. The organic layer was then distilled off under a reduced pressure to yield 76.9 mg (yield: 92.2%) of hydroxyethoxyarctigenin.

Mass analysis: ESI-MS/MS, m/z; 417.3 (M+H)$^+$
Molecular formula: $C_{23}H_{28}O_7$
In a $^1$H-NMR spectrum thereof, main chemical shift peaks relative to CDCl$_3$ (standard substance) are as follows:
6.82 (d, 1H), 6.75 (d, 1H), 6.68 (d, 1H), 6.63 (dd, 1H), 6.55 (dd, 1H), 6.48 (s, 1H), 4.11 (dd, 1H), 4.09 (t, 2H), 3.92 (dd, 2H), 3.88 (dd, 1H), 3.86, 3.82, 3.81, (3S, 9H), 2.94 (t, 2H), 2.81 (t, 1H), 2.48-2.66 (m, 4H)

Example 17

Hydroxypropoxyarctigenin

Into 2 mL of DMF were dissolved 75 mg (0.2 mmol) of arctigenin and 113.4 mg (1.2 mmol) of 3-chloro-1-propanol. Thereto was further added 165.9 mg (1.2 mmol) of potassium carbonate to cause the reactive components to react with each other at 100° C. for 3 hours. The reaction liquid was filtrated, and then the filtrate was distilled off under a reduced pressure. To the residue were added ethyl acetate and water, and this system was stirred. The organic layer was then distilled off under a reduced pressure to yield hydroxypropoxyarctigenin.

Example 18

Hydroxybutoxyarctigenin

Into 2 mL of DMF were dissolved 75 mg (0.2 mmol) of arctigenin and 130.3 mg (1.2 mmol) of 4-chloro-1-butanol. Thereto was further added 165.9 mg (1.2 mmol) of potassium carbonate to cause the reactive components to react with each other at 100° C. for 3 hours. The reaction liquid was filtrated, and then the filtrate was distilled off under a reduced pressure. To the residue were added ethyl acetate and water, and this system was stirred. The organic layer was then distilled off under a reduced pressure to yield hydroxybutoxyarctigenin.

Example 19

Hydroxypentoxyarctigenin

Into 2 mL of DMF were dissolved 75 mg (0.2 mmol) of arctigenin and 147.1 mg (1.2 mmol) of 5-chloro-1-pentanol. Thereto was further added 165.9 mg (1.2 mmol) of potassium carbonate to cause the reactive components to react with each other at 100° C. for 3 hours. The reaction liquid was filtrated, and then the filtrate was distilled off under a reduced pressure. To the residue were added ethyl acetate and water, and this system was stirred. The organic layer was then distilled off under a reduced pressure to yield hydroxypentoxyarctigenin.

Example 20

Hydroxyhexoxyarctigenin

Into 2 mL of DMF were dissolved 75 mg (0.2 mmol) of arctigenin and 163.9 mg (1.2 mmol) of 6-chloro-1-hexanol. Thereto was further added 165.9 mg (1.2 mmol) of potassium carbonate to cause the reactive components to react with each other at 100° C. for 3 hours. The reaction liquid was filtrated, and then the filtrate was distilled off under a reduced pressure. To the residue were added ethyl acetate and water, and this system was stirred. The organic layer was then distilled off under a reduced pressure to yield hydroxyhexoxyarctigenin.

Example 21

Hydroxyheptoxyarctigenin

Into 2 mL of DMF were dissolved 75 mg (0.2 mmol) of arctigenin and 234.1 mg (1.2 mmol) of 7-bromo-1-heptanol. Thereto was further added 165.9 mg (1.2 mmol) of potassium carbonate to cause the reactive components to react with each other at 100° C. for 3 hours. The reaction liquid was filtrated, and then the filtrate was distilled off under a reduced pressure. To the residue were added ethyl acetate

Example 22

Hydroxyoctoxyarctigenin

Into 2 mL of DMF were dissolved 75 mg (0.2 mmol) of arctigenin and 197.6 mg (1.2 mmol) of 8-chloro-1-n-octanol. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield hydroxyoctoxyarctigenin.

Example 23

Methoxyarctigenin

Into 2 mL of DMF were dissolved 75 mg (0.2 mmol) of arctigenin and 170.3 mg (1.2 mmol) of methyl iodide. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield methoxyarctigenin.

Example 24

Ethoxyarctigenin

Into 2 mL of DMF were dissolved 75 mg (0.2 mmol) of arctigenin and 187.2 mg (1.2 mmol) of ethyl iodide. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield ethoxyarctigenin.

Example 25

Propoxyarctigenin

Into 2 mL of DMF were dissolved 75 mg (0.2 mmol) of arctigenin and 147.6 mg (1.2 mmol) of 1-bromopropane. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield propoxyarctigenin.

Example 26

Butoxyarctigenin

Into 2 mL of DMF were dissolved 75 mg (0.2 mmol) of arctigenin and 164.4 mg (1.2 mmol) of 1-bromobutane. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield butoxyarctigenin.

Example 27

Pentoxyarctigenin

Into 2 mL of DMF were dissolved 75 mg (0.2 mmol) of arctigenin and 181.2 mg (1.2 mmol) of 1-bromopentane. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield pentoxyarctigenin.

Example 28

Hexoxyarctigenin

Into 2 mL of DMF were dissolved 75 mg (0.2 mmol) of arctigenin and 144.7 mg (1.2 mmol) of 1-chlorohexane. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield hydroxyhexoxyarctigenin.

Example 29

Heptoxyarctigenin

Into 2 mL of DMF were dissolved 75 mg (0.2 mmol) of arctigenin and 161.6 mg (1.2 mmol) of 1-chloroheptane. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield heptoxyarctigenin.

Example 30

Octoxyarctigenin

Into 2 mL of DMF were dissolved 75 mg (0.2 mmol) of arctigenin and 178.4 mg (1.2 mmol) of 1-chlorooctane. Thereto was further added 165.9 mg (1.2 mmol) of potassium carbonate to cause the reactive components to react with each other at 100° C. for 3 hours. The reaction liquid was filtered, and then the filtrate was distilled off under a reduced pressure. To the residue were added ethyl acetate and water, and this system was stirred. The organic layer was then distilled off under a reduced pressure to yield octoxyarctigenin.

The compounds synthesized in the working examples, and arctigenin as a comparison were used to evaluate the respective activities thereof.

Comparative Example 1

Palmitate Arctigenin

Into 10 mL of chloroform were dissolved 75 mg (0.2 mmol) of arctigenin and 48.5 mg (0.2 mmol) of palmitic acid. Thereto were further added 76.68 mg (0.4 mmol) of the water-soluble carbodiimide and 48 mg (0.4 mmol) of DMAP to cause the reactive components to react with each other in chloroform at room temperature for 6 hours. Water was added to the reaction liquid, and this system was stirred. The organic layer was then washed with 1 N HCL and saturated NaHCO$_3$ solution in water. The chloroform layer was distilled off under a reduced pressure to yield 90.6 mg of palmitate arctigenin.

Molecular formula: $C_{37}H_{54}O_7$ 6.92 (d, 1H), 6.76 (d, 1H), 6.74 (d, 1H), 6.66 (dd, 1H), 6.53 (dd, 1H), 6.49 (d, 1H), 4.17 (dd, 1H), 3.90 (dd, 1H), 3.85 (s, 3H), 3.82 (s, 3H), 3.75 (S, 3H), 2.97 (m, 2H), 2.54-2.56 (m, 6H), 1.75 (q, 2H), 1.25 (m, 24H), 0.88 (t, 3H)

(Evaluation on Production Inhibition of Endothelin-1 (ET-1))

Figure 2:
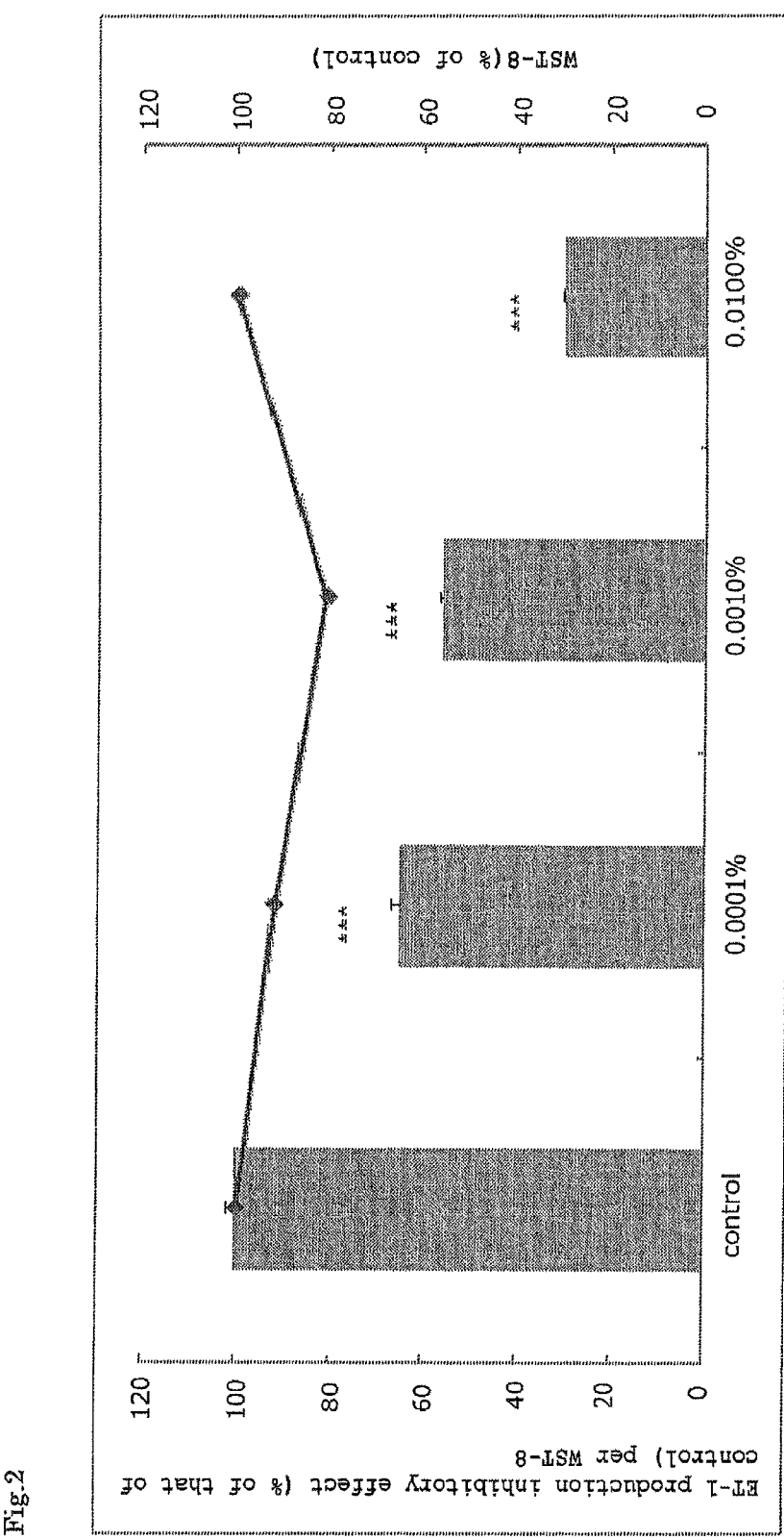
FIG. 2 is a graph showing an endothelin-1 production inhibitory effect of acetoxyarctigenin.
Figure 3:
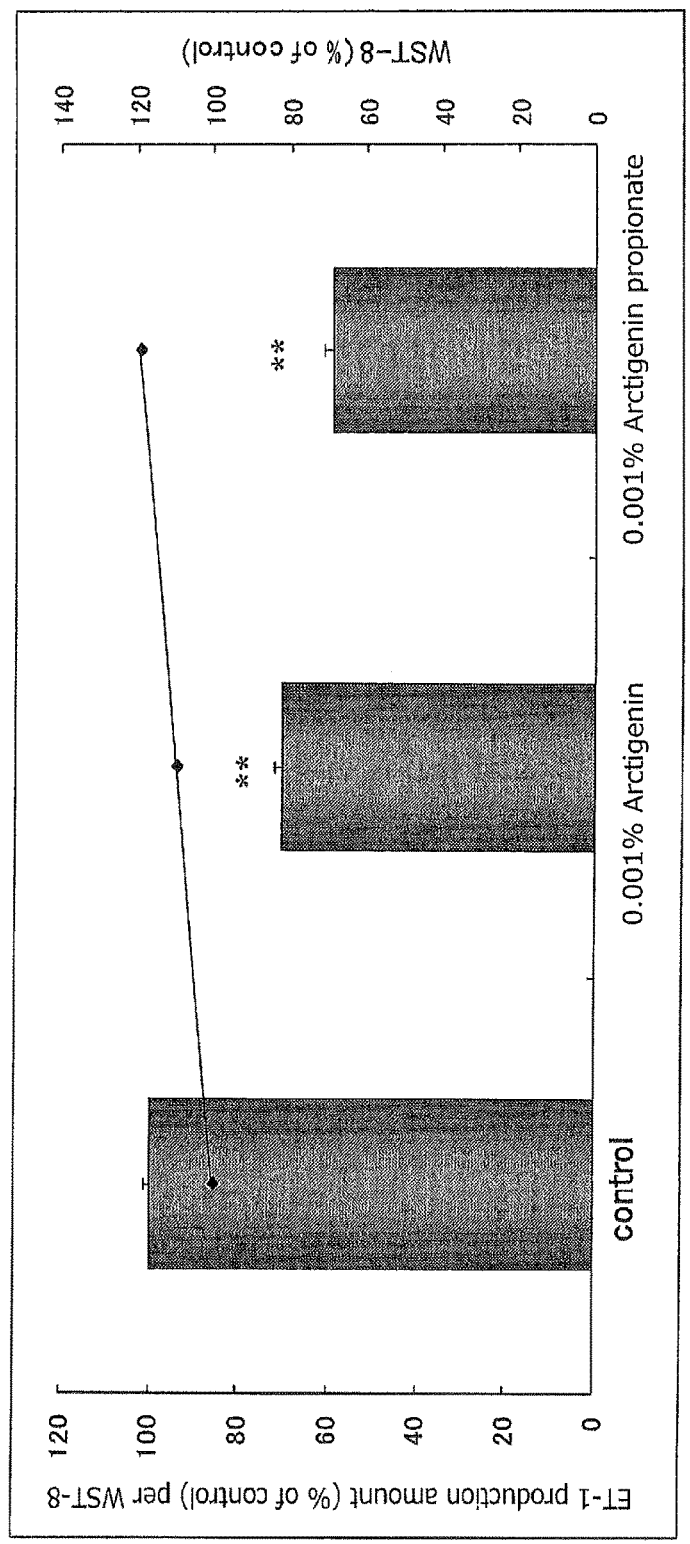
FIG. 3 is a graph showing an endothelin-1 production inhibitory effect of arctigenin propionate.
Figure 6:
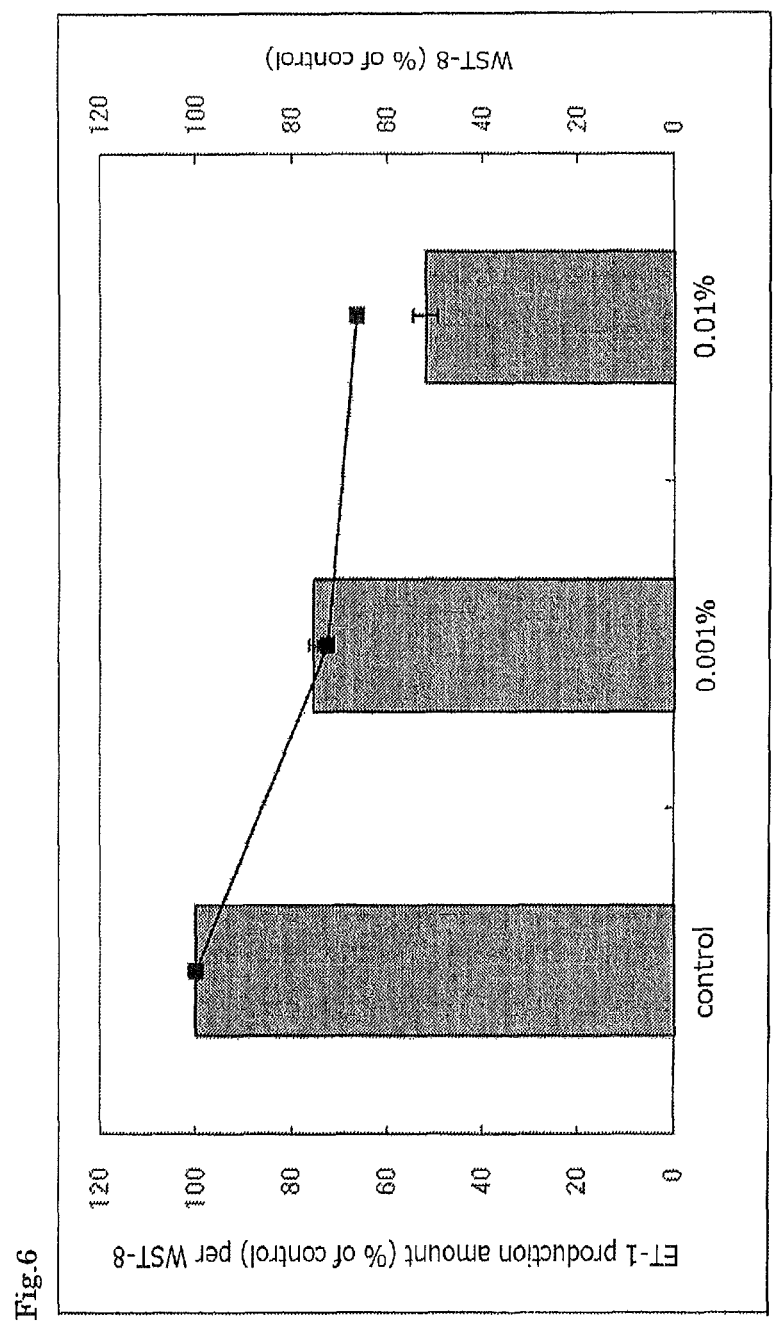
FIG. 6 is a graph showing an endothelin-1 production inhibitory effect of arctigenin hexanoate.
Figure 7:
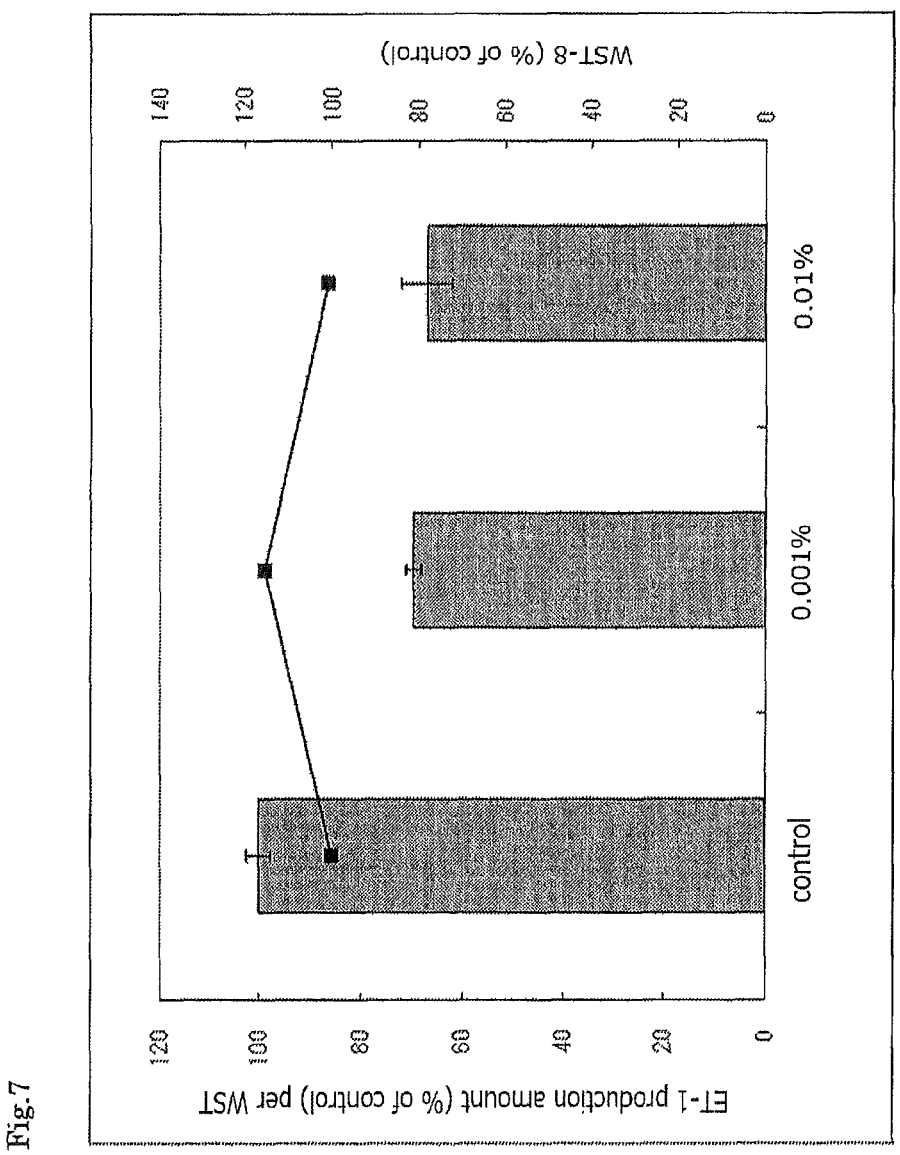
FIG. 7 is a graph showing an endothelin-1 production inhibitory effect of arctigenin nonanoate.
Figure 8:
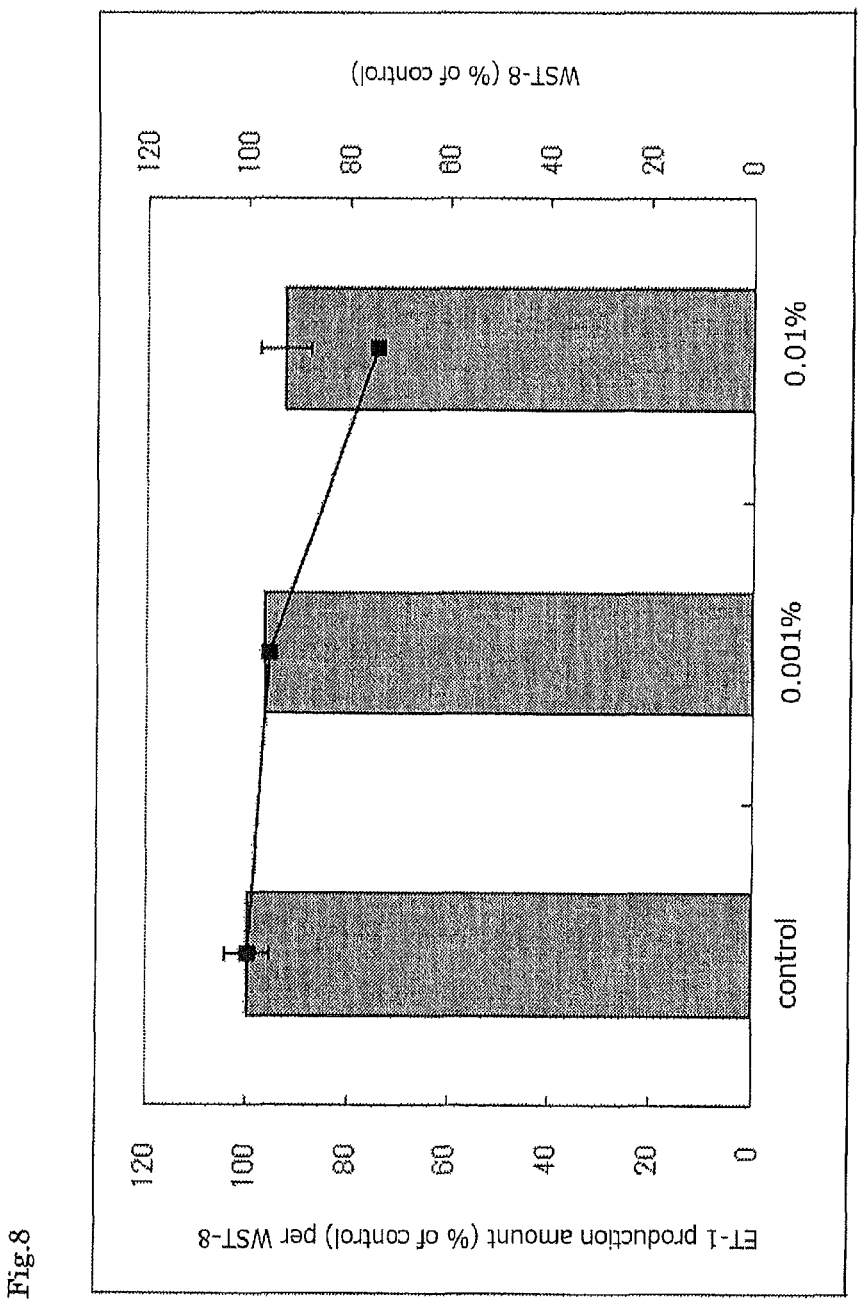
FIG. 8 is a graph showing an endothelin-1 production inhibitory effect of arctigenin palmitate.

Human epidermal keratinocytes were inoculated into 6-well plates to give an amount of 100000 cells per well, and then the cells were cultured for 3 days until the cells turned confluent. After it was verified that the cells turned confluent, their media were each substituted with PBS (−). The individual plates were irradiated with UVB at an irradiation intensity of 80 mJ/cm$^2$. After the irradiation with the UVB, DMEM in which arctigenin or each of the arctigenin derivatives was dissolved was added to one of the individual plates. After 48 hours from the irradiation, the supernatant (in the one plate) was collected, and the supernatant was centrifuged at 3000 rpm for 5 minutes. Furthermore, the supernatant therein was collected to prepare specimens for ELISA. As a control, a sample was used which was obtained by collecting a supernatant of an agent-free plate irradiated with UVB irradiation. A device used for measuring ET-1 was an Endthelin-1 Human EIA kit (manufactured by Assay Designs, Inc.). The respective absorbances of the specimens were measured at 450 nm, using a Cell Counting Kit-8 (manufactured by DOJINDO LABORATORIES), to evaluate the respective cell survival rates thereof. The results are shown in FIG. 1 (the compound of Example 16), FIG. 2 (the compound of Example 1), FIG. 3 (the compound of Example 2), FIG. 6 (the compound of Example 5), FIG. 7 (the compound of Example 8) and FIG. 8 (the compound of Comparative Example 1). In each of FIGS. 1 to 3 and FIGS. 6 to 8, one of its vertical axes represents a relative value of each of the specimens when the ET-1 production amount of the control was regarded as 100. In each of FIGS. 1 to 3 and FIGS. 6 to 8, its graph line represents the respective cell survival rates (of the specimens) when the value of the control was regarded as 100%.

As a result, it has been understood that the arctigenin derivatives of the present invention significantly inhibit the production of ET-1 from human epidermal keratinocytes, have no cell toxicity, and keep the number of the cells, which is evident from the FIGS. 1 to 3 and FIGS. 6 to 7. However, as is evident from FIG. 8, the compound of Comparative Example 1 does not significantly inhibit the production of ET-1 from human epidermal keratinocytes.

(Elastase Activity Measurement)

Into a 96-well plate were added 1 µL of each of the samples that was dissolved in DMSO, and 100 µL of elastase (derived from human leukocyte) adjusted to 10 µg/mL. Furthermore, to each of the wells was added to 50 µL of a substrate solution (Suc-(Ala)3-pNa) adjusted to 5 mM. A tris-HCL buffer (pH: 8.0) was used to adjust the final volume thereof to 200 µL. Under a condition at 37° C., the plate was heated for 2 hours. The absorbance of the sample at 405 nm was used as an index of the elastase activity, and the elastase inhibiting activity thereof was calculated in accordance with the following equation:

The elastase inhibiting activity (%)=(the absorbance of each of the samples/the absorbance of the control)×100

Figure 4:
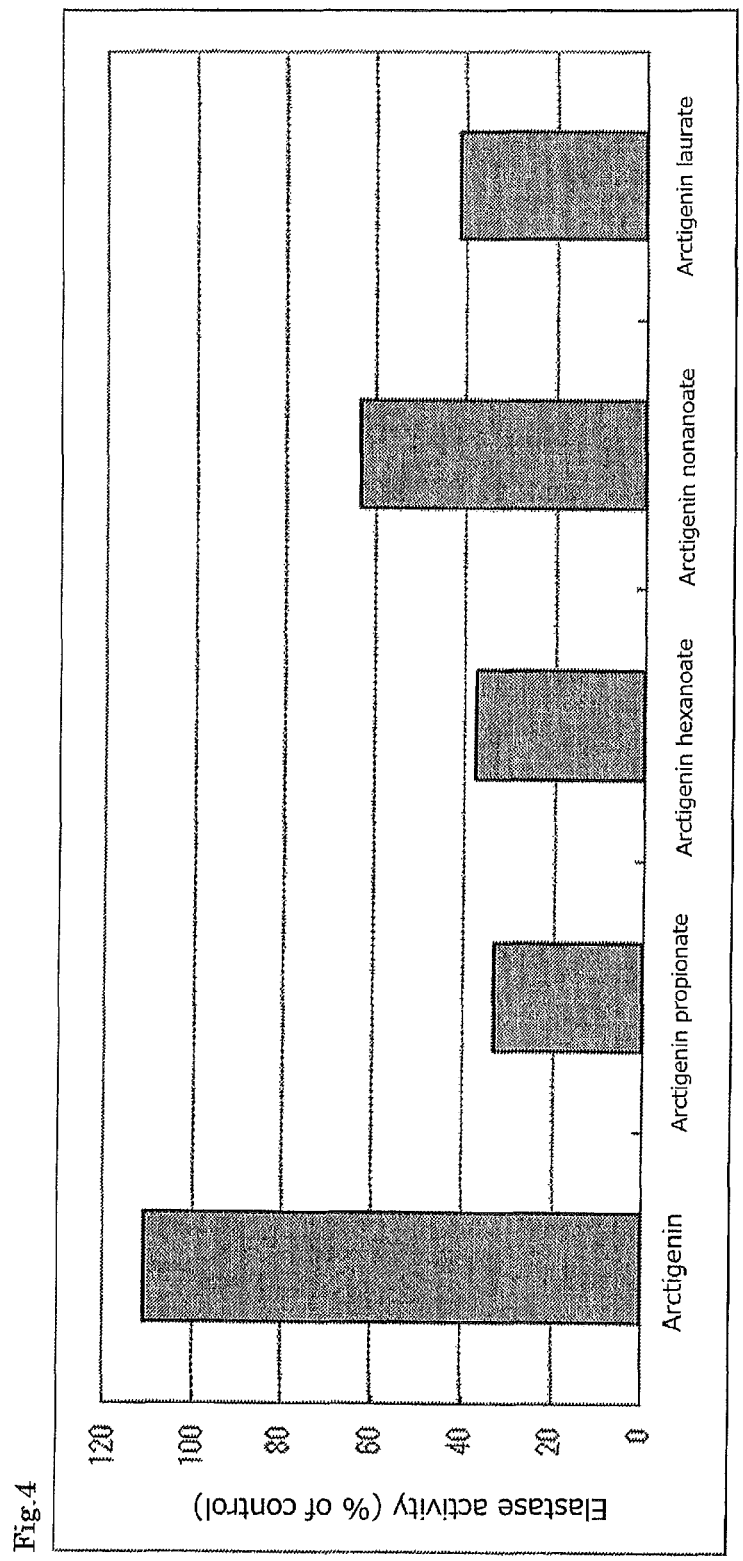
FIG. 4 is a graph showing respective elastase inhibiting activities of arctigenin derivatives, which are compared with that of arctigenin.
Figure 9:
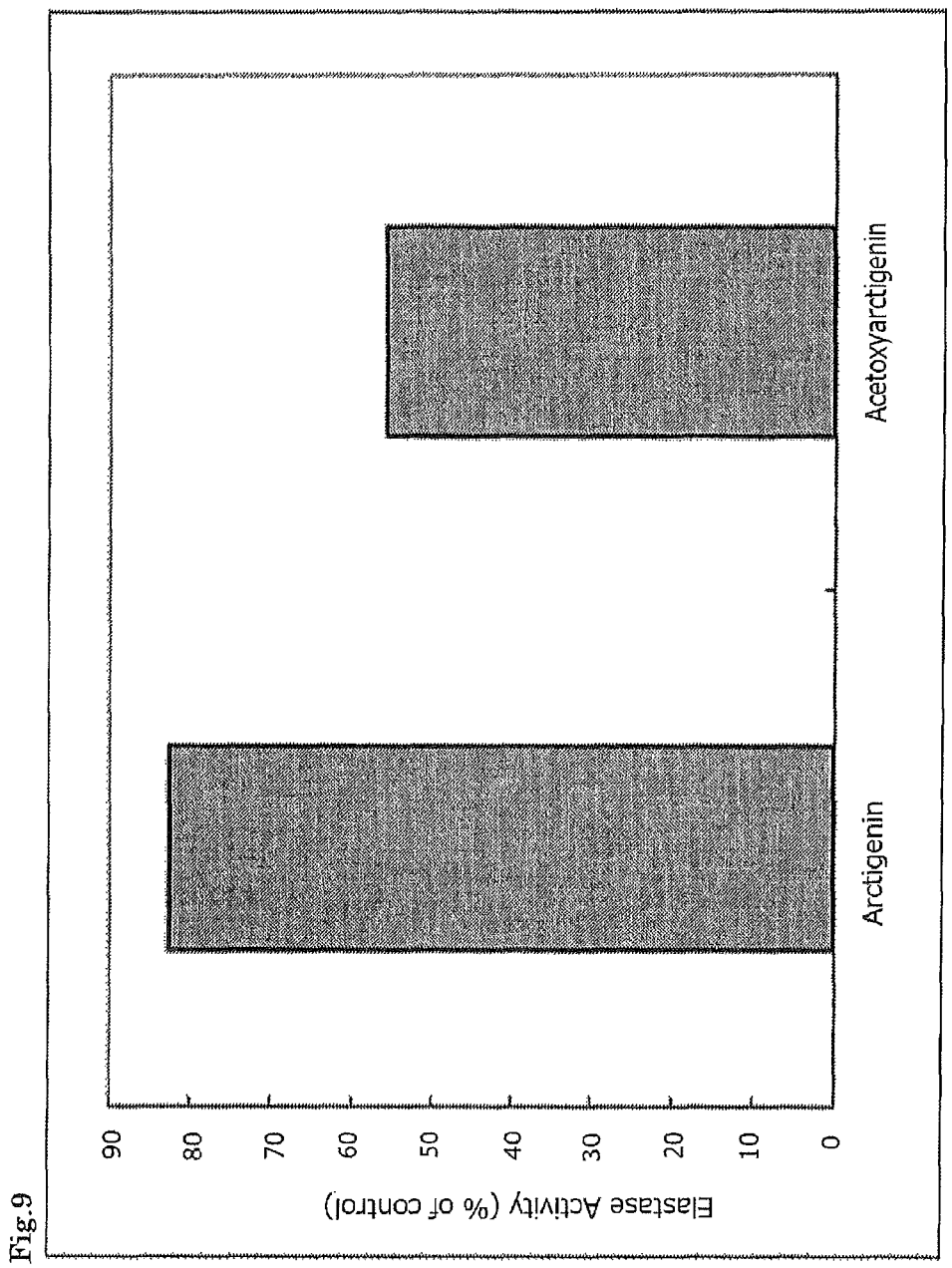
FIG. 9 is a graph showing the elastase inhibiting activity of acetoxyarctigenin, which is compared with that of arctigenin.

In this test, the respective elastase activities were measured. As a result, not only arctigenin propionate but also the alkylcarbonyl derivatives of arctigenin and acetoxyarctigenin showed a far stronger elastase inhibiting capability than arctigenin (FIGS. 4 and 9). Thus, this derivatization succeeded in yielding useful compounds capable of exhibiting a skin-whitening effect and further making a recovery from damages of skin cells by ultraviolet rays.

(Evaluating Example of Melanin Production Inhibition Test Using B16)

Cell Inoculation and Medicine Addition:

B16F10 melanoma cells were inoculated into a 6-well plate in an amount of 50,000 cells/cm$^2$. The cells were then cultured in a 0.005%-theophylline-containing DMEM medium at 37° C. under a 5%-CO$_2$-containing condition. After 24 hours, the culture solution was removed. Each of the following three was added thereto: arctigenin and arctigenin propionate that were each dissolved in a 0.005%-theophylline-containing DMEM to give a concentration of 0.1% (w/v); and only a 0.005%-theophylline-containing DMEM as a control. Furthermore, the cells were cultured for 72 hours.

Measurement of the Number of Cells, and Quantitative Determination of Melanin

Figure 5:
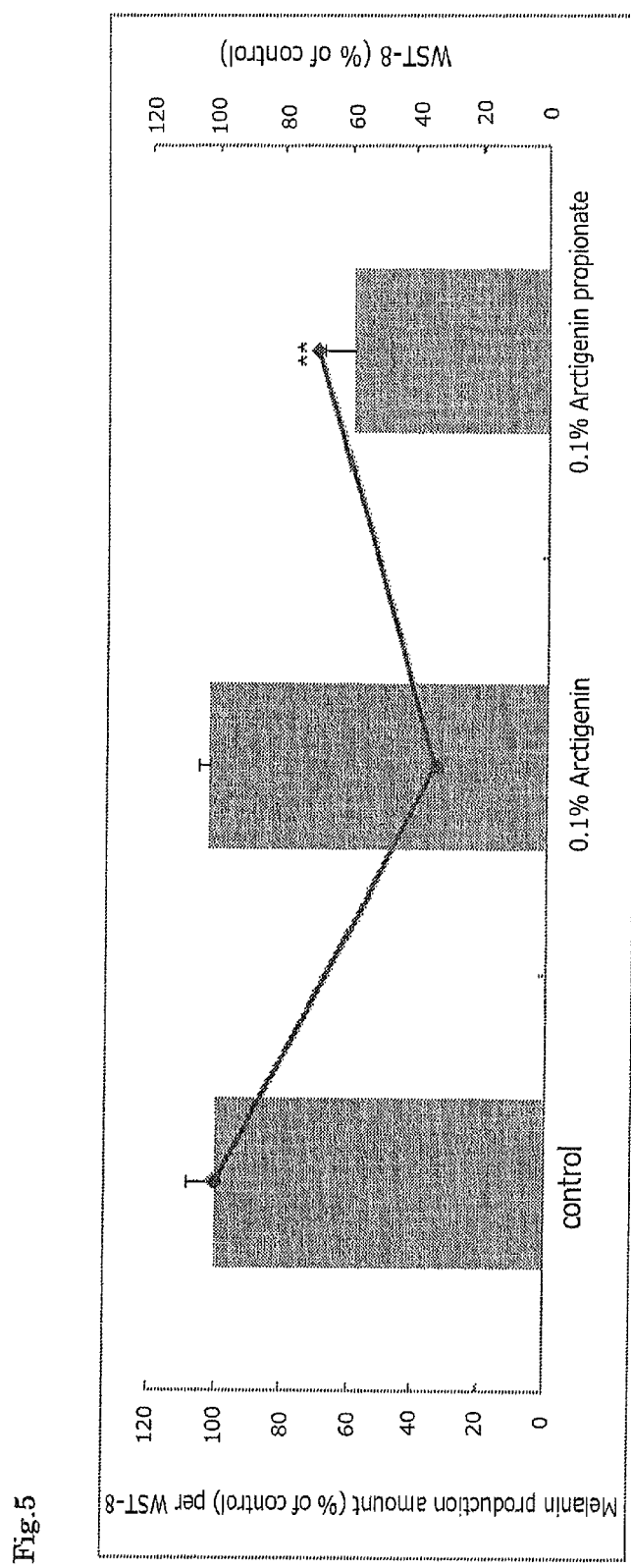
FIG. 5 is a graph showing the melanin production inhibited amount of arctigenin propionate, which is compared with that of arctigenin.

After the culturing for the 72 hours, the culture solution was removed (from each of the resultants), and then a WST-8 solution was added to the individual wells to culture the cells for one hour. After the culturing for one hour, 150 µL of the supernatant was collected, and then shifted into a 96-well plate. A microplate reader was used to measure the absorbance of the resultant sample at 450 nm. The absorbance of the control was regarded as 100%; and in this case, the cell survival rate of the sample was calculated. After the measurement of the cell survival rate, the culture solution was removed, and then the cells were washed two times with 1 mL of PBS (−). Thereafter, thereto was added 150 µL of a 2 N NaOH solution, and then the cells were dissolved at 60° C. for one hour. After one hour, 100 µL of the cell-dissolved liquid was shifted into a 96-well plate. The absorbance thereof was measured at 475 nm. The absorbance of the control was regarded as 100%; and in this case, the melanin amount of the sample was calculated. The above-mentioned cell survival rate was evaluated by measuring the absorbance of the sample at 450 nm, using a Cell Counting Kit-8 (manufactured by DOJINDO LABORATORIES). The results are shown in FIG. 5. In FIG. 5, one of its vertical axes represents respective relative values of the samples when the melanin production amount of the control was regarded as 100. In FIG. 5, its graph line represents the respective cell survival rates when the rate of the control was regarded as 100% (n=3). According to FIG. 5, the compound of Example 2 (arctigenin propionate) more significantly inhibited the production of melanin per living cell than arctigenin, and further this compound was also made lower in cell toxicity by the derivatization.

(Tyrosinase Inhibiting Activity Measurement)

To each well of a 96-well plate were added 1 μL of a 1 w/w % of each of the samples (test concentration: 0.01%) that was dissolved in DMSO, 20 μL of a 400 U/mL of a tyrosinase solution (originating from mushroom), and 79 μL of distilled water. Thereto were added a reaction solution (0.1 mg/mL L-tyrosine solution (Wako Pure Chemical Industries, Ltd.)) and 100 μL of a 1.3-mM copper sulfate pentahydrate solution (Wako Pure Chemical Industries, Ltd.)/a 60-mM phosphate buffer (pH: 6.0). The resultant was incubated at 37° C. for one hour. Thereafter, the absorbance of the sample was measured at 640 nm. This was used as a measured value (testing sample measured value or control measured value).

The tyrosinase inhibiting activity (%)=(the absorbance of each of the samples/the absorbance of the control)×100

Figure 10:
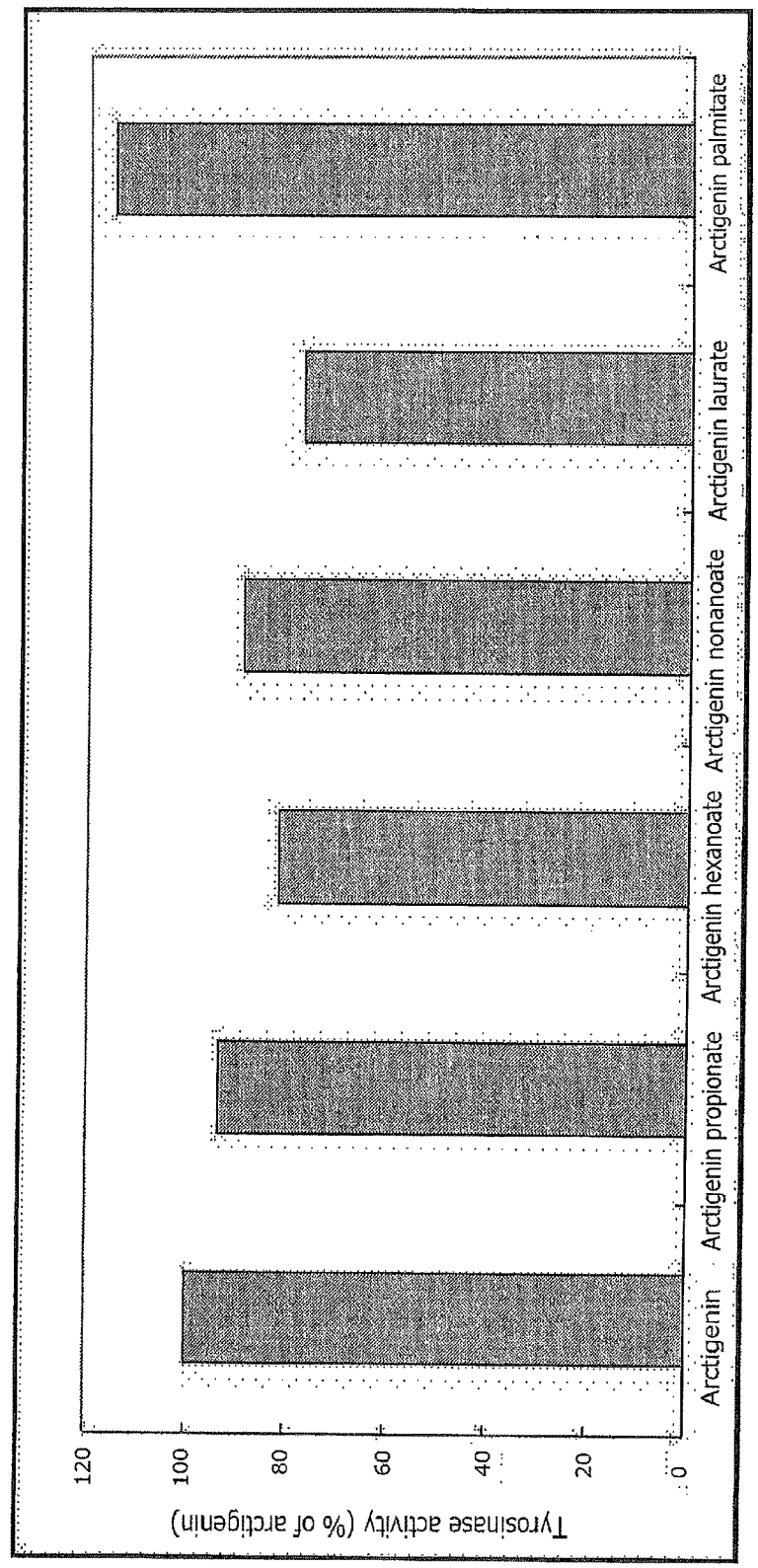
FIG. 10 is a graph showing respective tyrosinase activities of arctigenin derivatives, which are compared with that of arctigenin.

According to this test, the tyrosinase activity of each of the derivatives was measured. As a result, the derivative showed a stronger tyrosinase inhibiting capability than arctigenin. However, only arctigenin palmitate of Comparative Example 1 had no tyrosinase inhibiting capability (FIG. 10).

Composition Preparation Example 1

Cosmetic Compositions

Cosmetic compositions described below are prepared. The unit for any numerical value in each of the formulation examples is "% by weight".

The arctigenin derivatives described below each denote one of the compounds synthesized in the above-mentioned working examples.

TABLE 1

| Face lotion for skin-whitening | (W/W %) |
| --- | --- |
| Arctigenin propionate | 0.1 |
| Glycerin | 3 |
| 1,3-Butylene glycol | 5 |
| Polyoxyethylene hydrogenated castor oil | 0.3 |
| Chelating agent | 0.1 |
| Preservative | 0.1 |
| pH adjuster | Proper quantity |
| Perfume | 0.1 |
| Water | Proper quantity |
| Total | 100 |

TABLE 2

| Cream for preventing wrinkles | (W/W %) |
| --- | --- |
| Hydroxyethoxyarctigenin | 0.5 |
| Glycerin | 3 |
| 1,3-Butylene glycol | 5 |
| Sorbitan monostearate | 1 |
| Polyoxyethylene hydrogenated castor oil | 2 |
| Alkyl acrylate and methacrylate copolymer | 0.5 |
| Behenyl alcohol | 1 |

TABLE 2-continued

| Cream for preventing wrinkles | (W/W %) |
| --- | --- |
| Chelating agent | 0.1 |
| Preservative | 0.1 |
| Sodium hydroxide (10% solution in water) | Proper quantity |
| Perfume | 0.1 |
| Water | Proper quantity |
| Total | 100 |

Composition Preparation Example 2

Composition for Internal Use

TABLE 3

| Tablet | Parts by weight (mg) |
| --- | --- |
| Acetoxyarctigenin | 30 |
| Sodium croscarmellose | 120 |
| Crystalline cellulose | 240 |
| Lactose | 764 |
| Low-substitution-degree hydroxypropylcellulose (LHP) | 40 |
| Magnesium stearate | 6 |
| Total | 1200 |

These components were formulated into a composition in accordance with Pharmaceutical Preparation, General Rules "Tablet" in the Japanese Pharmacopeia; and then a pharmaceutical preparation was produced in the form of tablets each containing 380 mg of the composition. About the pharmaceutical preparation, two of the tablets are orally taken into an adult per day.

About this tablet-type pharmaceutical preparation, two tablets thereof may be taken in at each of three mealtimes per day.

The invention claimed is:

1. A method for skin whitening in a subject having skin in need of the skin whitening, comprising applying to the skin of the subject an arctigenin derivative represented by the following formula:

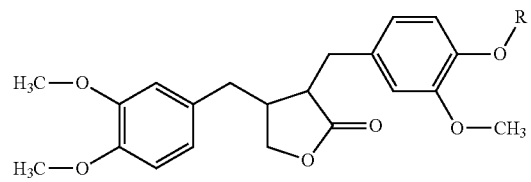

wherein R represents a $C_1$ to $C_{15}$ alkyl, a $C_1$ to $C_{14}$ alkylcarbonyl, or a hydroxy($C_1$ to $C_{15}$)alkyl.

2. The method for skin whitening of claim 1, wherein said arctigenin derivative is a tyrosinase inhibitor.

3. A method for inhibiting inflammation in a subject in need of inhibition of the inflammation, comprising administering to the subject an arctigenin derivative represented by the following formula:

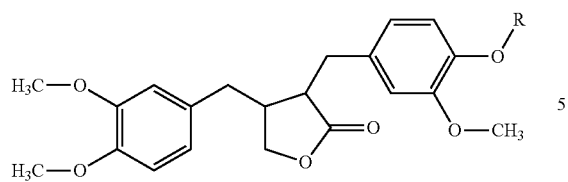
wherein R represents a $C_1$ to $C_{15}$ alkyl, a $C_1$ to $C_{14}$ alkylcarbonyl, or a hydroxy($C_1$ to $C_{15}$)alkyl.
4. The method for inhibiting inflammation of claim 3, wherein said arctigenin derivative is an endothelin-1 production inhibitor.
* * * * *